US012643841B2

(12) United States Patent
　　Olayiwola et al.

(10) Patent No.: US 12,643,841 B2
(45) Date of Patent: Jun. 2, 2026

(54) OXYGEN REMOVAL FROM AN ETHANE ODH PRODUCT STREAM USING ETHANOL

(71) Applicant: NOVA CHEMICALS (INTERNATIONAL) S.A., Fribourg (CH)

(72) Inventors: Bolaji Olayiwola, Calgary (CA); Vasily Simanzhenkov, Calgary (CA); Shahin Goodarznia, Calgary (CA); David Gent, Lacombe (CA); Mohammad Keshtkar, Calgary (CA)

(73) Assignee: NOVA CHEMICALS (INTERNATIONAL) S.A., Fribourg (CH)

( * ) Notice: Subject to any disclaimer, the term of this patent is extended or adjusted under 35 U.S.C. 154(b) by 285 days.

(21) Appl. No.: 18/684,746

(22) PCT Filed: Aug. 23, 2022

(86) PCT No.: PCT/IB2022/057902
　　§ 371 (c)(1),
　　(2) Date: Feb. 19, 2024

(87) PCT Pub. No.: WO2023/031733
　　PCT Pub. Date: Mar. 9, 2023

(65) Prior Publication Data
　　US 2024/0368058 A1　　Nov. 7, 2024

Related U.S. Application Data

(60) Provisional application No. 63/238,559, filed on Aug. 30, 2021.

(51) Int. Cl.
　　*C07C 5/48*　　　　(2006.01)
　　*C07C 7/148*　　　　(2006.01)

(52) U.S. Cl.
　　CPC ............ *C07C 5/48* (2013.01); *C07C 7/14841* (2013.01)

(58) Field of Classification Search
　　CPC ......... C07C 5/48; C07C 7/14841; C07C 7/12; C07C 7/148; C07C 7/14891; C07C 51/25;
　　　　　　　(Continued)

(56) References Cited

U.S. PATENT DOCUMENTS

| | | | |
|---|---|---|---|
| 10,343,957 B2 | 7/2019 | Serhal et al. | |
| 2019/0284116 A1* | 9/2019 | Lin ............................ | C07C 7/12 |

FOREIGN PATENT DOCUMENTS

| | | |
|---|---|---|
| WO | WO2017/144584 | 8/2017 |
| WO | WO2018/007912 | 1/2018 |

(Continued)

OTHER PUBLICATIONS

International Search Report & Written Opinion issued in corresponding International Application No. PCT/IB2022/057902, dated Dec. 13, 2022.

*Primary Examiner* — Ali Z Fadhel
(74) *Attorney, Agent, or Firm* — NORTON ROSE FULBRIGHT US LLP

(57)　　　　　ABSTRACT

A method and a system for converting ethane to ethylene are provided. An exemplary method includes providing a feed stream including the ethane and oxygen to an oxidative dehydrogenation reactor and converting at least a portion of the ethane to ethylene in the oxidative dehydrogenation reactor to provide a reactor effluent stream including ethane, ethylene, and oxygen, acetylene, or both. The method includes cooling the reactor effluent stream to form a cooled effluent stream and providing the cooled effluent stream to an oxygen removal reactor including an ODH catalyst bed.

(Continued)

A deoxygenation stream including water and an alcohol is provided to the oxygen removal reactor to form a deoxygenated effluent.

23 Claims, 5 Drawing Sheets

(58) Field of Classification Search
CPC ............ C07C 2523/20; C07C 2523/22; C07C 2523/28; C07C 2523/72; C07C 2523/80; C07C 2527/057; C07C 9/06; C07C 11/04; C07C 53/08; B01J 2523/00; B01J 2523/17; B01J 2523/27; B01J 2523/48; B01J 2523/55; B01J 2523/56; B01J 2523/64; B01J 2523/68
See application file for complete search history.

(56) References Cited

FOREIGN PATENT DOCUMENTS

| WO | WO-2019175731 A1 * | 9/2019 | ............... C07C 5/48 |
|----|----|----|----|
| WO | WO2020/079639 | 4/2020 | |
| WO | WO2021/019347 | 2/2021 | |
| WO | WO2021/038374 | 3/2021 | |
| WO | WO2021/124004 | 6/2021 | |
| WO | WO-2022002884 A1 * | 1/2022 | ............... C07C 5/48 |

* cited by examiner

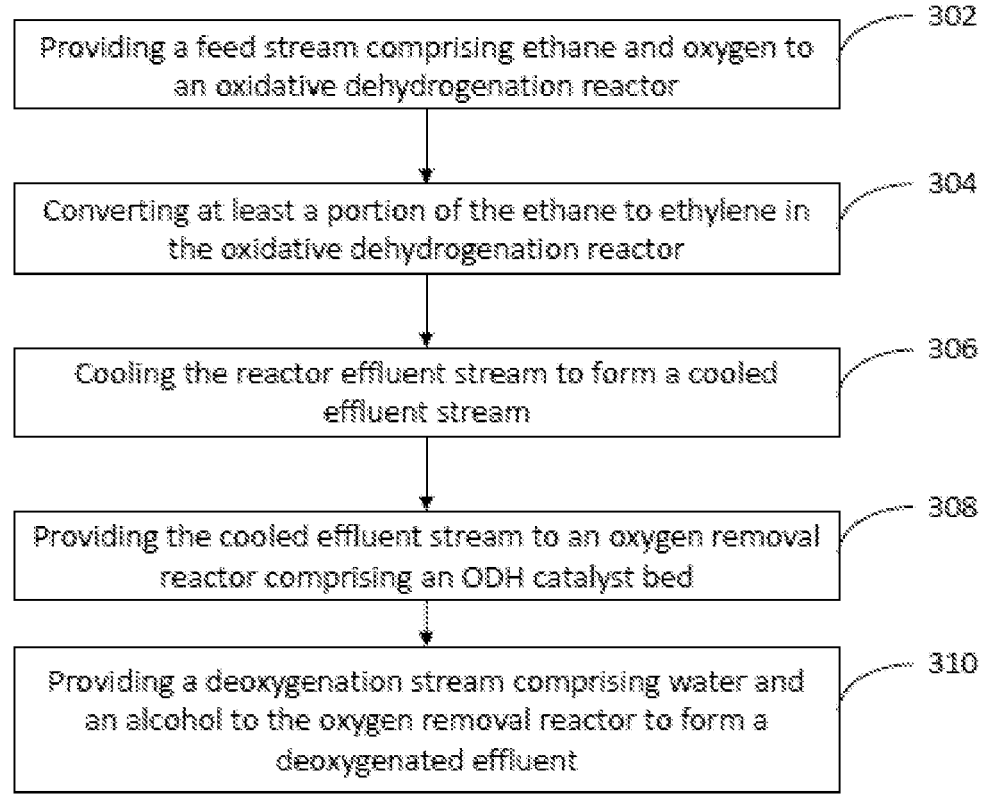

Providing a feed stream comprising ethane and oxygen to an oxidative dehydrogenation reactor — 302

Converting at least a portion of the ethane to ethylene in the oxidative dehydrogenation reactor — 304

Cooling the reactor effluent stream to form a cooled effluent stream — 306

Providing the cooled effluent stream to an oxygen removal reactor comprising an ODH catalyst bed — 308

Providing a deoxygenation stream comprising water and an alcohol to the oxygen removal reactor to form a deoxygenated effluent — 310

300

400

500

OXYGEN REMOVAL FROM AN ETHANE ODH PRODUCT STREAM USING ETHANOL

CROSS-REFERENCE TO RELATED APPLICATION

This application is a national phase application under 35 U.S.C. § 371 of International Application No. PCT/IB2022/057902, filed Aug. 23, 2022, which claims priority to and the benefit of U.S. Provisional Application No. 63/238,559, filed Aug. 30, 2021. The contents of the referenced patent applications are incorporated into the present application by reference.

TECHNICAL FIELD

The present invention relates generally to oxidative dehydrogenation (ODH) of ethane into ethylene. More specifically, the present invention relates to an ODH process that includes multiple reactors in series for the removal of oxygen, acetylene, or both from product streams.

BACKGROUND ART

Olefins like ethylene, propylene, and butylene, are basic building blocks for a variety of commercially valuable polymers. Since naturally occurring sources of olefins do not exist in commercial quantities, polymer producers rely on methods for converting the more abundant lower alkanes into olefins. The method of choice for today's commercial scale producers is steam cracking, a highly endothermic process where steam-diluted alkanes are subjected very briefly to a temperature of up to about 900° C. The fuel demand to produce the required temperatures and the need for equipment that can withstand that temperature add significantly to the overall cost. In addition, the high temperature promotes the formation of coke, which accumulates within the system, resulting in the need for costly periodic reactor shut down for maintenance and coke removal.

Oxidative dehydrogenation (ODH) processes are an alternative to steam cracking that are exothermic and produce little or no coke. In ODH, a lower alkane, such as ethane, is mixed with oxygen in the presence of a catalyst and optionally an inert diluent, such as carbon dioxide, nitrogen, or steam, at temperatures as low as 300° C., to produce the corresponding alkene. Various other oxidation products may be produced in this process, including, but not limited to, carbon dioxide and acetic acid.

It is beneficial to operate an ODH reactor with at least a small amount of oxygen remaining in the reactor product stream. This is done to preserve the ODH catalyst from permanent damage or deactivation which is caused by exposing it to an oxygen-free reducing environment at elevated temperature.

For fixed bed ODH reactors, another reason to operate with at least a small amount of oxygen is to ensure that the entirety of the ODH catalyst bed is utilized, instead of only the more upstream regions of the catalyst bed, which can occur when the ODH product stream is less than 1 ppm $O_2$.

However, oxygen being present in the ODH product gas stream causes serious safety and operational issues in the downstream equipment, primarily at and downstream of the first compression stage of the ODH plant. As a result, there is a need to remove oxygen to a very low to non-detectable levels before the product gas compression.

There are a number of different approaches disclosed in the patent and public literature, with the main emphasis on catalytically combusting a small portion of the ODH product gas to the complete consumption of any residual oxygen. This approach is viable, however is highly undesirable since it increases overall oxygen consumption in the ODH process and reduces overall process selectivity toward ethylene.

SUMMARY OF INVENTION

An embodiment described in examples herein provides a method of converting ethane to ethylene. The method includes providing a feed stream including ethane and oxygen to an oxidative dehydrogenation reactor and converting at least a portion of the ethane to ethylene in the oxidative dehydrogenation reactor to provide a reactor effluent stream including the ethane, ethylene, and oxygen, acetylene, or both. The method includes cooling the reactor effluent stream to form a cooled effluent stream and providing the cooled effluent stream to an oxygen removal reactor including an ODH catalyst bed. A deoxygenation stream including water and an alcohol is provided to the oxygen removal reactor to form a deoxygenated effluent.

Another embodiment described in examples herein provides a system for forming ethane from ethylene. The system includes an oxidative dehydrogenation (ODH) reactor, a first heat exchanger to cool an ODH effluent from the ODH reactor, and an oxygen removal reactor including an ODH catalyst.

BRIEF DESCRIPTION OF DRAWINGS

FIG. 3 is a process flow diagram of a method for converting ethane to ethylene and removing oxygen from the effluent.

DESCRIPTION OF EMBODIMENTS

Figure 1:
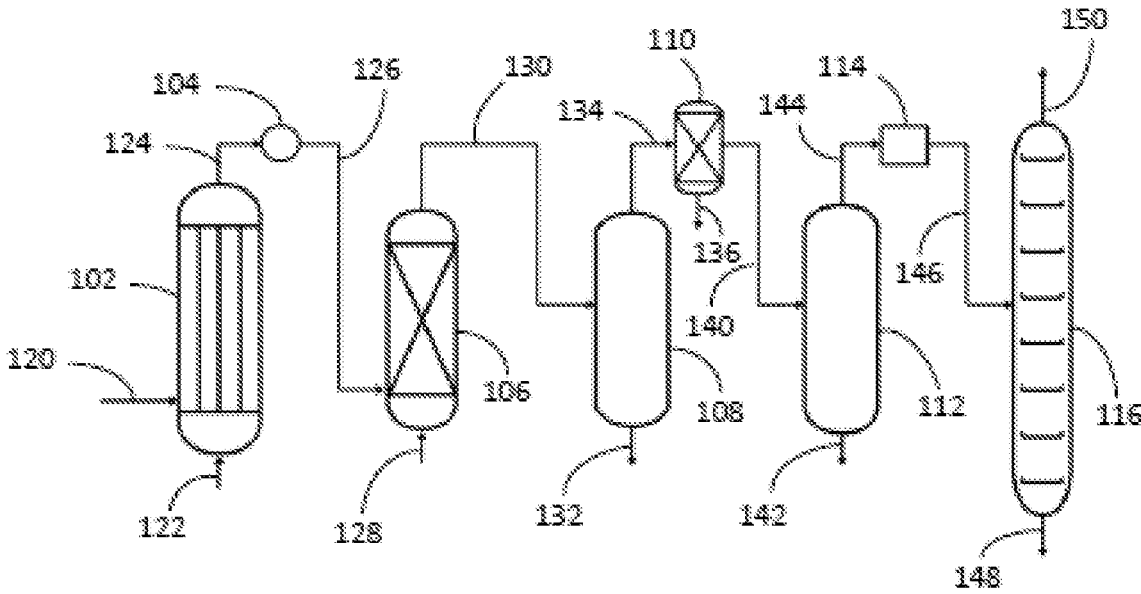
FIG. 1 is a simplified block diagram of an oxidative dehydrogenation (ODH) process unit.

Ethane undergoes oxidative dehydrogenation at temperatures of between about 300° C. and about 450° C. to produce ethylene and other byproducts such as steam, acetic acid, $CO_2$ and CO. The catalyst used for this is generally a mixture of metal oxides, such as $MoVNbTeO_x$. Exposure of the catalyst to a reducing environment, e.g., including only hydrocarbons, may lead to reduction of the catalyst to either a mixture of metals or a mixture of metals and metallic carbides, resulting in loss of activity. Thus, the oxygen content of the gas stream leaving the reactor is maintained at about 0.1 mol. %, or 1000 ppm on a dry basis to avoid deactivating the catalyst.

However, unreacted oxygen in the reactor effluent stream may be problematic for operations in downstream equipment, such as the amine tower where the presence of oxygen can result in amine degradation. Further, unreacted oxygen may cause fouling in downstream product gas compressors. In addition, the unreacted oxygen may be cause undesirable reactions, for example, causing peroxides formation, among other reactions. Thus, it is desirable to remove all, or most, of the unreacted oxygen as possible from the ODH product gas to minimize the issues mentioned.

Further, acetylene in the product stream may be problematic for downstream users. For example, acetylene may be a catalyst poison in some polymerization processes.

Embodiments described in examples herein provide methods and systems for removing unreacted oxygen and acetylene from an ODH product gas. The product stream from the main ODH reactor may be cooled to lower a temperature than the reaction temperature, such as from about 140° C. to about 170° C., from about 145° C. to about 165° C., from about 150° C. to about 160° C., or from about 150° C. to about 152° C. This stream is then fed into another reactor, termed an oxygen removal reactor herein. The oxygen removal reactor includes an ODH catalyst and an ethanol-water mix is combined with the product stream or is injected into the bed of the oxygen removal reactor.

The ODH catalyst used in the oxygen removal reactor may be the same as the ODH catalyst present in the main ODH reactor catalyst bed, or a different ODH catalyst may be used. The amount of ethanol injected depends on desired outcome, for example, the amount may be in excess of the stoichiometric amount used to completely react with the unreacted oxygen completely or in a quantity that will leave some unreacted oxygen in the product gas, for example, for use in subsequent reactions.

The deoxygenated stream from the oxygen removal reactor is passed through a scrubber, for example, to remove acetic acid. The process gas from the scrubber may be fed through a polishing unit to remove acetylene. In some embodiments, the polishing unit is a second oxygen removal reactor. For example, in some embodiments, the process gas is compressed and fed into a heat exchanger to raise its temperature to 150° C., which is the operating temperature of a catalyst used in the second oxygen removal reactor. For example, the catalyst may include a Cu/Zn oxide catalyst, among many others discussed herein. The chemosorbed oxygen on the Cu/Zn oxide catalyst selectively oxidizes CO and acetylene in the product stream to $CO_2$. The depleted bed then initiates a chemical reaction for the removal of the remaining trace amount of unreacted oxygen and acetylene in the gas stream, forming a polished gas stream. The polished gas stream may be passed through an amine column or a caustic column to remove $CO_2$.

Other than in the operating examples or where otherwise indicated, all numbers or expressions referring to quantities of ingredients, reaction conditions, etc. used in the specification and claims are to be understood as modified in all instances by the term "about". Accordingly, unless indicated to the contrary, the numerical parameters set forth in the following specification and attached claims are approximations that can vary depending upon the desired properties, which the present disclosure desires to obtain. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical values, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include all sub-ranges between and including the recited minimum value of 1 and the recited maximum value of 10; that is, having a minimum value equal to or greater than 1 and a maximum value of equal to or less than 10. Because the disclosed numerical ranges are continuous, they include every value between the minimum and maximum values. Unless expressly indicated otherwise, the various numerical ranges specified in this application are approximations.

Definitions

As used herein, the term "diluent" refers to a gas that forms a non-flammable mixture with hydrocarbons or oxidation gasses. In some instances, a diluent may be selected that participates in the ODH reaction in the presence of an ODH catalyst, such as carbon dioxide. Further, the diluent may be used to remove heat. In some embodiments, the diluent may also be used to ensure that the mixture of ethane and oxygen is outside of flammability limits.

As used herein, the term "essentially free of oxygen" means the amount of oxygen present, if any, remaining in a process stream as described herein, is low enough that it will not present a flammability or explosive risk to the downstream process streams or equipment. The amount of oxygen present is preferably below 10 ppm, more preferably below 5 ppm, most preferably below 1 ppm.

As used herein, the term "fixed bed reactor" refers to one or more reactors, in series or parallel, often including a cylindrical tube filled with catalyst pellets with reactants flowing through the bed and being converted into products. The catalyst in the reactor may have multiple configurations including, but not limited to, one large bed, several horizontal beds, several parallel packed tubes, and multiple beds in their own shells.

As used herein, the term "fluidized bed reactor" refers to one or more reactors, in series or parallel, often including a fluid (gas or liquid) which is passed through a solid granular catalyst, which can be shaped as tiny spheres (typically smaller than 200 μm), at high enough velocities to suspend the solid and cause it to behave as though it were a fluid.

As used herein, the term "linear velocity", in many cases the linear velocity of the gas stream (m/s), refers to the flow rate of a gas stream/cross-sectional surface area of the reactor/void fraction of the catalyst bed. In many cases the flow rate refers to the total of the flow rates of all the gases entering an ODH reactor and is measured where the oxygen and ethane first contact the ODH catalyst and at the temperature and pressure at that point. The cross-section of the reactor is also measured at the entrance of the ODH catalyst bed. The "void fraction" of the catalyst bed refers to the volume of voids in the catalyst bed/total volume of the catalyst bed. The "volume of voids" refers to the voids between catalyst particles and does not include the volume of pores inside the catalyst particles. In many instances, the linear velocity can range from 5 cm/sec to 1500 cm/sec, in some instances from 10 cm/sec to 500 cm/sec.

As used herein, the term "MoVOx catalyst" refers to a mixed metal oxide having the empirical formula $Mo_{6.5-7.0}V_3O_d$, where d is a number to at least satisfy the valence of the metals; a mixed metal oxide having the empirical formula $Mo_{6.25-7.25}V_3O_d$, where d is a number to at least satisfy the valence of the metals, or combinations thereof.

As used herein, the term, "oxidative dehydrogenation" or "ODH" refers to processes that couple the endothermic dehydrogenation of ethane with the strongly exothermic oxidation of hydrogen as is further described herein.

As used herein, the term "substantially free of acetylene" means the amount of acetylene present, if any, remaining in a process stream as described herein, is undetectable using the analytical techniques described herein or zero ppmv.

ODH Process Unit

FIG. 1 is a simplified block diagram of an ODH process unit 100. The ODH process unit may be constructed as a standalone chemical complex or may be part of a larger chemical complex, such as a refinery or polymerization plant. In some embodiments, the chemical complex, shown in one embodiment schematically in FIG. 1, includes, in cooperative arrangement, an ODH reactor 102, a heat exchanger 104, an oxygen removal reactor 106, a quench tower or acetic acid scrubber 108, a polishing unit 110, an amine wash tower 112, a drier 114, and a distillation tower 116. The ODH reactor 102 includes at least one ODH catalyst capable of catalyzing, in the presence of oxygen, which may be introduced via an oxygen line 120, the oxidative dehydrogenation of ethane introduced via an ethane line 122. Although the polishing unit 110, which may be a second oxygen removal reactor or an acetylene adsorption bed, is shown directly after quench tower or acetic acid scrubber 108, it can be placed further downstream, as described with respect to FIG. 2. In many cases, the process configuration can be more energy efficient if the polishing unit 110 is placed after the input stream has been compressed.

In various embodiments, the ODH process for the oxidative dehydrogenation of ethane is conducted at a temperature in the ODH reactor 102 of between about 300° C. and about 500° C., or between about 300° C. and about 450° C., or between about 330° C. and about 425° C. In various embodiments, the ODH reactor 102 is operated at a pressure of between about 0.5 psig and about 100 psig (about 3.447 kPag and about 689.47 kPag), or between about 15 psig and about 50 psig (about 103.4 kPag and about 344.73 kPag). In various embodiments, the residence time of the ethane in the ODH reactor 102 is between about 0.12 seconds and about 9 seconds, or between about 1 second and about 3.6 seconds.

In some embodiments, the process has a selectivity for the corresponding alkene, such as ethylene in the case of the ODH of ethane, of greater than about 85%, of greater than about 90%, of greater than about 95%, or greater than about 98%. In various embodiments, the gas hourly space velocity (GHSV) is between about 400 h$^{-1}$ and about 30000 h$^{-1}$, or between about 1000 h$^{-1}$ and about 3600 h$^{-1}$. In some embodiments, the gas velocity can be described in terms of weight hourly space velocity (WHSV). In various embodiments, the WHSV is between about 0.4 h$^{-1}$ and about 30 h$^{-1}$. In some embodiments the gas velocity can be described in terms of linear velocity, for example, between about 5 cm/sec and about 500 cm/sec. In some embodiments, the space-time yield of corresponding alkene (productivity) in g/hour per kg of the catalyst is at least about 50, or at least about 1500, or at least about 3000, or at least about 3500, at a temperature of the ODH reactor 102 of between about 330° C. to 500° C., depending on the temperature profile in the catalyst bed. In some embodiments, the productivity of the catalyst will increase with increasing temperature until the selectivity is decreased.

The ODH reaction may also occur in the presence of a diluent, such as carbon dioxide, nitrogen, or steam, that is added to ensure the mixture of oxygen and hydrocarbon are outside of flammability limits. As described herein, the diluent may (e.g., carbon dioxide or steam) or may not (e.g., nitrogen) participate in the ODH reaction. Determination of whether a mixture is outside of the flammability limits, for the prescribed temperature and pressure, is within the knowledge of the skilled worker.

The ODH reaction, and the oxygen removal reaction using an ODH catalyst, can be performed with any number of ODH catalysts. As mentioned herein, the catalyst used in the ODH reaction and the oxygen removal reaction may be the same or different. Non-limiting examples of a suitable oxidative dehydrogenation catalyst include those containing one or more mixed metal oxides selected from:

i) catalysts of the formula:

$$Mo_aV_bTe_cNb_dPd_eO_f$$

where a, b, c, d, e and f are the relative atomic amounts of the elements Mo, V, Te, Nb, Pd and O, respectively; and when a=1, b=0.01 to 1.0, c=0.01 to 1.0, d=0.01 to 1.0, 0.00≤ e≤0.10 and f is a number to at least satisfy the valence state of the metals in the catalyst;

ii) catalysts of the formula:

$$Ni_gA_hB_iD_jO_f$$

where g is a number from 0.1 to 0.9, in many cases from 0.3 to 0.9, in other cases from 0.5 to 0.85, in some instances 0.6 to 0.8; h is a number from 0.04 to 0.9; i is a number from 0 to 0.5; j is a number from 0 to 0.5; and f is a number to at least satisfy the valence state of the catalyst; A is chosen from Ti, Ta, V, Nb, Hf, W, Y, Zn, Zr, Si and Al or mixtures thereof; B is chosen from La, Ce, Pr, Nd, Sm, Sb, Sn, Bi, Pb, TI, In, Te, Cr, Mn, Mo, Fe, Co, Cu, Ru, Rh, Pd, Pt, Ag, Cd, Os, Ir, Au, Hg, and mixtures thereof; D is chosen from Ca, K, Mg, Li, Na, Sr, Ba, Cs, and Rb and mixtures thereof; and O is oxygen;

iii) catalysts of the formula:

$$Mo_aE_kG_lO_f$$

where E is chosen from Ba, Ca, Cr, Mn, Nb, Ta, Ti, Te, V, W and mixtures thereof; chosen from Bi, Ce, Co, Cu, Fe, K, Mg, V, Ni, P, Pb, Sb, Si, Sn, Ti, U, and mixtures thereof; a=1; k is 0 to 2; 1=0 to 2, with the proviso that the total value of 1 for Co, Ni, Fe and mixtures thereof is less than 0.5; and f is a number to at least satisfy the valence state of the metals in the catalyst;

iv) catalysts of the formula:

$$V_mMo_nNb_oTe_pMe_qO_f$$

where Me is chosen from Ta, Ti, W, Hf, Zr, Sb and mixtures thereof; m is from 0.1 to 3; n is from 0.5 to 1.5; o is from 0.001 to 3; p is from 0.001 to 5; q is from 0 to 2; and f is a number to at least satisfy the valence state of the metals in the catalyst; and v) catalysts of the formula:

$$Mo_aV_rX_sY_tZ_uM_vO_f$$

where X is at least one of Nb and Ta; Y is at least one of Sb and Ni; Z is at least one of Te, Ga, Pd, W, Bi and Al; M is at least one of Fe, Co, Cu, Cr, Ti, Ce, Zr, Mn, Pb, Mg, Sn, Pt, Si, La, K, Ag and In; a=1.0 (normalized); r=0.05 to 1.0; s=0.001 to 1.0; t=0.001 to 1.0; u=0.001 to 0.5; v=0.001 to 0.3; and f is a number to at least satisfy the valence state of the metals in the catalyst.

vi) a mixed metal oxide having the empirical formula:

$$Mo_{6.5-7.0}V_3O_d$$

where d is a number to at least satisfy the valence of the metals in the catalyst.

vii) a mixed metal oxide having the empirical formula:

$$MO_{6.25-7.25}V_3O_d$$

where d is a number to at least satisfy the valence of the metals in the catalyst.

In some embodiments, the catalyst may be supported on/agglomerated with a binder. Some binders include acidic, basic or neutral binder slurries of $TiO_2$, $ZrO_2$ $Al_2O_3$, AlO (OH) and mixtures thereof. Another useful binder includes $Nb_2O_5$. The agglomerated catalyst may be extruded into a suitable shape, such as rings, spheres, or saddles, among others, of a size typically used in fixed bed reactors. When the catalyst is extruded, various extrusion aids known in the art can be used. In some cases, the resulting support may have a cumulative surface area of less than 35 $m^2/g$ as measured by BET, in some cases, less than 20 $m^2/g$, in other cases, less than 3 $m^2/g$, and a cumulative pore volume from 0.05 to 0.50 $cm^3/g$.

The ODH reactor 102 may be a fixed bed or fluidized bed reactor. In some embodiments, the ODH reactor is a fixed bed reactor. In a fixed bed reactor, reactants are introduced into the reactor at one end, flow past an immobilized catalyst, products are formed and leave at the other end of the reactor. In some embodiments, the fixed bed reactor is a shell-and-tube reactor. Designing a fixed bed reactor suitable for the methods disclosed herein can follow techniques known for reactors of this type.

Additional embodiments include the use of a fluidized bed reactor, where the catalyst bed can be supported by a porous structure, or a distributor plate, located near a bottom end of the reactor and reactants flow through at a velocity sufficient to fluidize the bed (e.g. the catalyst rises and begins to swirl around in a fluidized manner). The reactants are converted to products upon contact with the fluidized catalyst and the reactants are subsequently removed from the upper end of the reactor. Design considerations those skilled in the art can modify and optimize include, but are not limited to, the shape of the reactor, the shape and size of the distributor plate, the input temperature, the output temperature, and reactor temperature and pressure control.

Embodiments of the disclosure include using a combination of both fixed bed and fluidized bed reactors, each with the same or different ODH catalyst. For example, in an embodiment, the oxygen removal reactor 106 has a similar size and configuration to the ODH reactor 102, allowing the two reactors to be interchanged.

The ODH reaction that occurs within the ODH reactor 102 may also produce a variety of other products which may include carbon dioxide, carbon monoxide, oxygenates, and water, depending on the catalyst and the prevailing conditions within the ODH reactor 102. These products leave the ODH reactor 102, along with unreacted ethane, ethylene, residual oxygen, carbon monoxide, and diluent, if added, via the ODH reactor product line 124.

The ODH reactor product line 124 is directed to the heat exchanger 104. In the heat exchanger 104, the reactor effluent is cooled, for example, from greater than 300° C. to less than 180° C. In some embodiments, the reactor effluent is between about 350° C. and 450° C., between about 375° C. and 425° C., or about 400° C. The cooled effluent stream leaves the heat exchanger 104 through a cooled effluent line 126. The cooled effluent stream is between about 140° C. and about 180° C., or between about 150° C. and about 160° C., or between about 151° C. and 155° C.

The cooled effluent line 126 directs the cooled effluent stream to the oxygen removal reactor 106. An ethanol line 128 adds a mixture of water and ethanol to the oxygen removal reactor 106. In various embodiments, the mixture of water and ethanol may be added to the ODH product line 124 prior to the heat exchanger 104. In various embodiments, the mixture of ethanol and water may be added to the cooled effluent stream prior to the oxygen removal reactor 106. The oxygen removal In various embodiments, the ethanol solution includes a concentration of ethanol between about 0.1 vol. % and about 50 vol. %, or between about 1 vol. % and about 35 vol. %, or between about 10 vol. % and about 20 vol. %. In an embodiment, the ethanol is at a concentration of about 13.5 vol. % in water.

In the oxygen removal reactor 106, the ethanol reacts with oxygen to at least partially remove the oxygen, as discussed in further detail below, to form a deoxygenated stream with reduced levels of oxygen. The oxygen removal reactor may be a fixed bed reactor.

In various embodiments, oxygen removal in oxygen removal reactor 106 is conducted at a temperature in the oxygen removal reactor 106 of between about 140° C. and about 180° C., or between about 150° C. and about 160° C., or between about 151° C. and about 155° C. In various embodiments, the oxygen removal reactor 106 is operated at a pressure of between about 0.5 psig and about 100 psig (about 3.447 kPag and about 689.47 kPag), or between about 15 psig and about 50 psig (about 103.4 kPag and about 344.73 kPag). In various embodiments, the residence time of the product stream in the oxygen removal reactor 106 is between about 0.12 seconds and about 9 seconds, or between about 1 second and about 3.6 seconds.

The deoxygenated stream is directed by a deoxygenated effluent line 130 to the quench tower or acetic acid scrubber 108, which quenches the products from the deoxygenated effluent line 130 and facilitates removal of acetic acid and water via the quench tower bottom outlet 132. The deoxygenated stream may be cooled prior to entering the quench tower or acetic acid scrubber 108, or the deoxygenated stream may be cooled in the quench tower by contact with a quenching agent such as water. Unconverted ethane, ethylene, unreacted oxygen, carbon dioxide, carbon monoxide, and inert diluent that are added to the quench tower or acetic acid scrubber 108 exit through quench tower overhead line 134 and are directed into the polishing unit 110.

In various embodiments, the polishing unit 110 is a second removal reactor, for example, using a catalyst system containing copper and zinc, which can catalyze the removal of acetylene and oxygen. In other embodiments, the polishing unit 110 is an acetylene adsorption bed, for example, including a copper or silver based adsorbent. The adsorbent or catalyst can include any number of copper or silver compounds that vary in activity. In various embodiments, the catalyst can include CuZnZr, AgCe, CuMn, CuCc, MnCe, and CrCe, among others. These catalysts can be supported on silica.

In various embodiments, the polishing unit 110 is operated at a temperature of between 60° C. and about 200° C., or between about 70° C. and about 150° C., or between about 80° C. and about 120° C. In various embodiments, the polishing unit 110 is operated at a pressure of between about 0.5 psig and about 100 psig (about 3.447 kPag and about 689.47 kPag), or between about 15 psig and about 50 psig (about 103.4 kPag and about 344.73 kPag). In various embodiments, the residence time of the product stream in the polishing unit 110 is between about 0.12 seconds and about 9 seconds, or between about 1 second and about 3.6 seconds.

In embodiments in which the polishing unit 110 is a second oxygen removal reactor, the second reactor contains a catalyst that includes a group 11 metal with an optional promoter and an optional support as described herein. The polishing unit may be a fixed bed reactor. The catalyst causes unreacted oxygen or a surface metal oxide to react with carbon monoxide to form carbon dioxide. In some embodiments, acetylene is removed by reaction with the unreacted oxygen or with a surface metal oxide. In the second reactor, most or all of the unreacted oxygen and acetylene remaining after the oxygen removal reactor 106 is consumed. All or a portion of the carbon dioxide in the second reactor can be recycled back to the ODH reactor 102 via recycle lines 136 and 138 to act as an oxidizing agent, diluent, or both, as described above. The remaining unconverted ethane, ethylene, unreacted oxygen (if present), all or part of the carbon dioxide, carbon monoxide (if present), and inert diluent are conveyed to amine wash tower 112 via wash tower feed line 140.

Any carbon dioxide present in the feed stream from the wash tower feed line 140 is captured in the amine wash tower 112 and removed via a carbon dioxide bottom outlet 142 and may be sold, or, alternatively, may be recycled back to the ODH reactor 102 as described above. Constituents other than carbon dioxide that are introduced into the amine wash tower 112 via wash tower feed line 140, leave the amine wash tower 112 through an amine wash tower overhead line 144, and are passed through the dryer 114 before being directed to the distillation tower 116 through a dry feed line 146. In the distillation tower 116, a cryogenic distillation is performed to isolate C2/C2+ hydrocarbons for removal via C2/C2+ hydrocarbons bottom outlet 148. The remainder includes mainly C1 hydrocarbons, including remaining inert diluent and carbon monoxide (if any), which leave the distillation tower 116 via an overhead stream 150 which may be flared, burned to create heat (e.g. in a gas fired furnace), or directed to an oxygen separation module as described in U.S. Pat. No. 10,343,957, assignee NOVA Chemicals (International) S.A.

The C2/C2+ hydrocarbons removed from bottom outlet 148 may be directed to a splitter to separate ethylene from ethane. In an embodiment the distillation tower 116 is capable of separating the C2/C2+ hydrocarbons fraction into ethane and ethylene fractions, where the ethylene may be withdrawn from a side outlet (not shown) of the distillation tower and the ethane may be withdrawn from the bottom outlet 148 of the distillation tower. The ethane fraction, derived from either a splitter or from a distillation tower capable of separating ethane from ethylene, may be recycled back to the reactor and the ethylene fraction can be used in additional processes (e.g. for production of ethylene oxide) or can be used to make polyethylene.

In some embodiments, a concern for ODH processes is the mixing of a hydrocarbon with oxygen. Under certain conditions, the mixture may be unstable and lead to an explosive event. Mixers may be used to mix a hydrocarbon containing gas with an oxygen containing gas in a flooded mixing vessel. By mixing in this way, pockets of unstable compositions are surrounded by a non-flammable liquid so that even if an ignition event occurred it would be quenched immediately. The result is a non-flammable and homogeneous mixture of hydrocarbon and oxygen gases that are provided to the ODH reactor. Examples of gas mixers suitable for use with the methods and systems described herein can be found in PCT patent applications WO 2018/007912 and WO 2021/019347, assignee NOVA Chemicals (International) S.A.

In some embodiments, a flooded gas mixer is disposed upstream of the ODH reactor 102. In this instance, the oxygen line 120 and the ethane line 122 are fed into flooded gas mixer. A homogeneous mixture that includes hydrocarbon and oxygen, and optionally a diluent, can be introduced into the ODH reactor 102 from the flooded gas mixer via a mixture line. An oxygen enriched stream from an oxygen separation module may feed directly into the flooded gas mixer or in combination with the oxygen line 120 into the flooded gas mixer.

Figure 2:
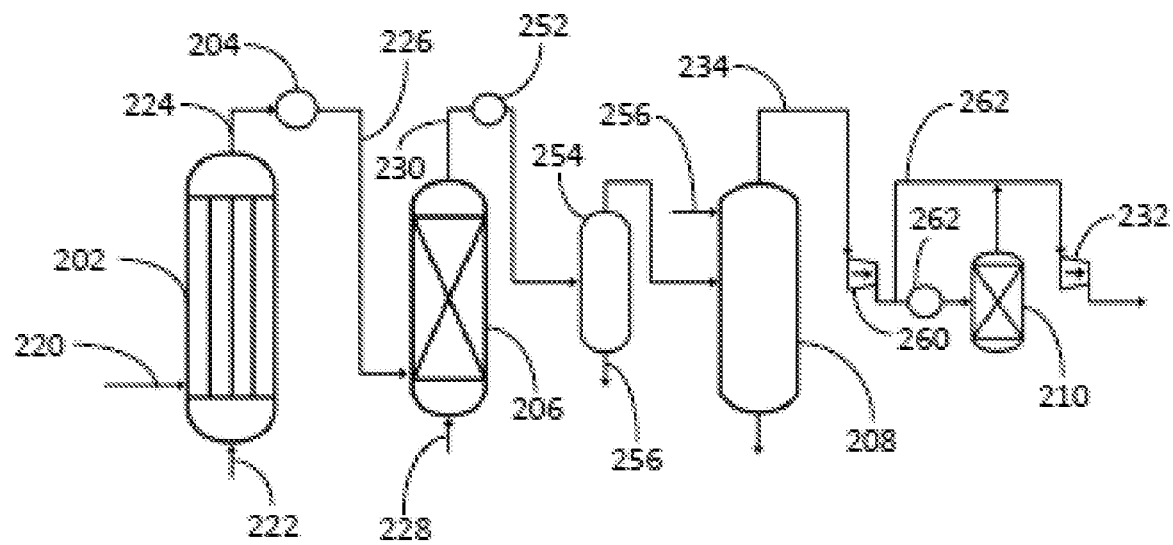
FIG. 2 is a simplified block diagram of a process unit for removing oxygen and acetylene in an oxygen removal reactor.

FIG. 2 is a simplified block diagram of a process unit 200 for removing oxygen and acetylene in an oxygen removal reactor. Like numbered items are as described with respect to FIG. 1. Referring to FIG. 2, the process unit 200, like process unit 100, generally includes an ODH reactor 202, a heat exchanger 204, an oxygen removal reactor 206, and a quench tower or acetic acid scrubber 208. Process unit 200, like process unit 100, may also include downstream separation components including the amine wash tower, drier, distillation tower, and option oxygen separation module, which are not shown in FIG. 2 for simplicity.

The ODH reactor 202 includes at least one ODH catalyst capable of catalyzing, in the presence of oxygen, which may be introduced via an oxygen line 220, the oxidative dehydrogenation of ethane introduced via an ethane line 222, to produce a product stream comprising unconverted ethane, ethylene, unconverted oxygen, acetic acid, water, and possibly acetylene. As described herein, the ODH product stream is conveyed from the ODH reactor 202 to a heat exchanger 204 by the ODH reactor product line 224. In some embodiments, the product stream is cooled to lower a temperature than the reaction temperature, for example, between about 140° C. to about 170° C., about 145° C. to about 165° C., about 150° C. to about 160° C., or about 150° C. and about 152° C. This stream is then fed by the cooled effluent line 226 into the oxygen removal reactor 206.

The oxygen removal reactor 206 contains an ODH catalyst bed and an ethanol/water stream is injected into the bed via ethanol line 228. Alternatively, the ethanol/water mix may be combined with the product stream either before or after the heat exchanger 204. The ODH catalyst may be the same as in the ODH reactor or may be selected to optimize the oxygen removal reaction. The amount of ethanol injected depends on desired outcome. For example, the amount injected can be in excess of the stoichiometric amount required to completely remove the unreacted oxygen. A lower amount may be injected to leave some unreacted oxygen in the process gas. The injected ethanol may be converted to acetic acid in a reaction with oxygen, or, in the absence of oxygen, the excess ethanol may be dehydrated to form ethylene. Use of alternative alcohols, such as propanol, may be used in place of ethanol. However, it should be noted that use of propanol would likely result in the production of propanoic acid (in the present of residual oxygen) or propylene (in the absence of residual oxygen).

In this embodiment, the effluent of the oxygen removal reactor 206 is fed into a cooler 252 by the deoxygenated effluent line 230, where the temperature of the effluent is dropped below the dew point of acetic acid and water. As a result, a substantial amount of the acetic acid and water in the stream is condensed. A flash drum 254 is used to separate the liquid stream from the gas stream. The liquid stream may be removed as a bottom stream 256 which may be further processed in an acetic acid separation system (not shown) to separate the acetic acid from the water.

The gas stream from the flash drum 254 is fed into scrubber 208 to remove any trace amount of acetic acid with a countercurrent flow of water, added through a water line 256. The remaining gases, including unconverted ethane, ethylene, unreacted oxygen, carbon dioxide, carbon monoxide, and inert diluent that are added to scrubber 208 exit through quench tower overhead line 234 and are compressed in a compressor 260. The compressed process gas may be treated based on the acetylene content. If the acetylene gas content is high enough to make downstream hydrogenation economical, for example, greater than about 5%, greater than about 10%, or higher, a bypass line 262 may be used to bypass the polishing step. If the acetylene is too low to make separation economically feasible, the compressed process gas may be fed to a polishing unit to remove traces of acetylene and oxygen. In the embodiment portrayed in FIG. 2, the polishing unit is a second oxygen removal reactor 222. The compressed process gas is fed into a heat exchanger 264 to raise its temperature to between about 80° C. and about 250° C., or about 150° C., which is the operating temperature of the catalyst bed containing a Cu/Zn oxides catalyst in the second oxygen removal reactor 210. The chemosorbed oxygen on the Cu/Zn oxides catalyst selectively oxidizes CO in the product stream to $CO_2$. The depleted bed then initiates a chemical reaction for the removal of the remaining trace amount of unreacted oxygen and acetylene in the gas phase. Alternatively, if all the unreacted oxygen from the ODH reactor 202 was removed in the oxygen removal reactor 206, and Cu/Zn oxides catalyst is to be used for acetylene removal by combustion in the second bed, oxygen must be supplied to the bed, for example, through an oxygen line (not shown). As described herein, the second oxygen removal reactor 210, in the polishing unit may be replaced with an acetylene adsorbent bed, for example, containing an adsorbent containing Cu, Ag, or both. In this case, acetylene in the product stream gets adsorbed on the adsorbent bed because of the high affinity of acetylene for the adsorbent. The adsorbent bed can then be periodically taken out of service for regeneration.

The polished gas (or bypass gas) may be compressed again in a second compressor 232 before being fed to the downstream separation system, including an amine wash tower, drier, and distillation tower. Final processing results in an ethylene stream 248 that can then be used to make polyethylene or other ethylene derived products. C1 hydrocarbons may be flared, used to heat a furnace, or passed through an oxygen separation module as described above. Recaptured ethane may be recycled and added to the ODH reactor 202.

FIG. 3 is a process flow diagram of a method 300 for converting ethane to ethylene and removing oxygen from the effluent. The method 300 begins at block 302 by providing a feed stream comprising the ethane and oxygen to an oxidative dehydrogenation reactor. At block 304, at least a portion of the ethane is converted to ethylene in the oxidative dehydrogenation reactor to provide a reactor effluent stream comprising ethane, ethylene, and oxygen, acetylene, or both. At block 306, the reactor effluent stream is cooled to form a cooled effluent stream. At block 308, the cooled effluent stream is provided to an oxygen removal reactor comprising an ODH catalyst bed. At block 310, a deoxygenation stream comprising water and an alcohol is provided to the oxygen removal reactor to form a deoxygenated effluent.

The present disclosure also contemplates use of various tools commonly used for chemical reactors, including flowmeters, compressors, valves, and sensors for measuring parameters such as temperature and pressure. It is expected that the person of ordinary skill in the art would include these components as deemed necessary for operation or for compliance with legal obligations related to safety regulations.

EXAMPLES

The following examples are non-limiting and are only intended to demonstrate, by physical experimentation in combination with computer modeling, the removal of or reduction in oxygen and acetylene in ethane ODH product streams. The person skilled in the art would appreciate that variations of the components described may accomplish similar results in reducing oxygen and acetylene levels in ethane ODH product streams.

Preparation of the ODH Test Catalyst

An ODH catalyst having the general composition $Mo_1V_{0.30-0.40}Te_{0.10-0.20}Nb_{0.10-0.20})O_{4-14}$ was prepared as follows: A solution of $(NH_4)_6Mo_7O_{24} \cdot 4H_2O$ (44.20 g, 35.77 mmol, white solid) in 600 mL of distilled water was prepared in a 2 L round bottom flask equipped with a magnetic stir bar. A solution of $VOSO_4 \cdot 3.46H_2O$ (14.07 g, 62.95 mmol, bright blue solid) in 600 mL of distilled water was prepared in a 1-L beaker equipped with a magnetic stir bar. Both solutions were stirred in a 60° C. water bath until homogeneous. The blue vanadium solution was then added to the clear colorless molybdenum solution. This resulted in a dark purple solution with a fine suspension. Sodium dodecyl sulfate (SDS) (13.57 g, 47.06 mmol, white solid) was added to the reaction mixture. The purple slurry was left to stir at 60° C. for 1 hour.

The reaction mixture was transferred to a glass liner, with a total volume of about 1380 mL measured after rinsing. The liner was loaded into a 2-L pressure reactor (Parr Instrument Company, Moline, IL) and the gap filled with distilled water. The reactor was sealed and the head space evacuated and backfilled with nitrogen gas 10× times. The headspace was left under 15 psig nitrogen gas and sealed. The reactor was transferred to a programmable oven and heated for 24 hours at 230° C. (1-hour ramp to 230° C., 24-hour cooling ramp back to room temperature). Once cooled to room temperature, the reactor was vented, and the contents filtered using a Buchner funnel and 4 quantitative filter papers. The oily mother liquor was decanted off and the filter papers changed. The filter cake was rinsed with 1250 mL of distilled water. The filtrate was a dark blue color and the product was a charcoal/grey purple color.

The filter cake was dried in an oven at 90° C. overnight with 15.29 g of product being recovered (37% estimated yield). The uncalcined catalyst was broken up with a spatula and then loaded into a programmable muffle furnace. The program was set to ramp over one hour to 280° C. and held there for 9 hours, before cooling back to room temperature naturally. This air treated product was ground with mortar and pestle and submitted for CHN analysis. The carbon and nitrogen content was found to be less than 1 wt. %. The material was loaded into a quartz boat and centered in the quartz tube of the QRU furnace. The quartz tube was purged (400 sccm) with nitrogen for 8 hours, after which the nitrogen feed was fed through an oxygen scrubbing bed to further purify the nitrogen to less than 0.25 ppmv oxygen. This ultra-high purity (UHP) nitrogen was purged through the quartz tube overnight. The next morning, the furnace was turned on and heated to 400° C. over a 4-hour ramp. The catalyst was calcined at 400° C. for 2 hours and then cool to ambient temperature naturally.

Preparation of the Cu/Zn Oxides Catalyst

A Cu/Zn oxides catalyst, the reduced form of an oxide precursor composition containing 70 wt. % CuO, 20 wt. % ZnO and 10 wt. % $ZrO_2$, was prepared as follows: a Cu—Zn—Zr nitrate solution (metal content 15.2 wt. %, a Cu:Zn:Zr ratio corresponding to a $CuO:ZnO:ZrO_2$ weight ratio of 7:2:1) was precipitated with ammonium hydroxide solution (28-30 wt. % ammonia) at pH 6.5 and 70° C. After completion of precipitation, the suspension was stirred for a further 120 minutes at pH 6.5 and 70° C. Next, the solution was filtered, and the filter cake washed free of nitrate with demineralized water and dried at 120° C. The dried powder was calcined at 300° C. for 240 minutes in a forced air oven.

Example 1 (Removal of Residual $O_2$ with Ethanol)

Removal of residual oxygen from an ODH product stream was demonstrated using a fixed bed reactor unit (FBRU) consisting of two fixed bed reactors in series, each reactor comprising a SS316L stainless steel tube having a 1" O.D. and 34' length and wrapped in a water/steam jacket for temperature control. Both reactors were packed with the ODH test catalyst and operated as an oxygen removal bed at a temperature of about 151° C. to about 153° C. The reactors were fed simulated mixtures of ODH process effluent, including ethylene, ethane, oxygen, and acetylene, along with an ethanol-water mixture. The combined feed composition, on both a dry basis and liquid basis (Table 1A) was added at a gas hourly space velocity (GHSV) of 648 h$^{-1}$.

For the FBRU experiments, GC analyzers were used for identifying the gas product effluent and liquid product effluent. The GC analyzers have a general detection limit of 0.01% and were calibrated at least once a month to ensure accuracy of the data. For experiments at which a detected compound was close to the detection limit (<0.1), the corresponding GC chromatogram was manually analyzed to determine if the chromatogram reflect noise pattern or a clear peak pattern. Only if the peak pattern was observed, then the value was accepted, otherwise it was assumed to be zero. The reaction was continued for a duration of 29 hour and 45 minutes. Product gas compositions after three intervals are shown in Table 1B, with $O_2$ content dropping to zero. The liquid composition, assessed on a condensed fraction downstream of the fixed bed reactors, was measured at the end of the experimental time frame.

TABLE 1A

Feed Gas Composition as a Function of Elapsed Time

| Feed Gas Composition (dry basis - vol. %) | | | | Feed Liquid Composition (vol. %) | | |
|---|---|---|---|---|---|---|
| $C_2H_6$ | $C_2H_4$ | $O_2$ | $CO_2$ | $C_2H_5OH$ | $H_2O$ | $CH_3COOH$ |
| 11.0 | 87.9 | 0.6 | 0.6 | 13.6 | 85.9 | 0 |

TABLE 1B

Product Gas Composition as a Function of Elapsed Time

| Elapsed Time | Product Gas Composition (dry basis - vol. %) | | | | Product Liquid Composition (vol. %) | | |
|---|---|---|---|---|---|---|---|
| (hr:min) | $C_2H_6$ | $C_2H_4$ | $O_2$ | $CO_2$ | $C_2H_5OH$ | $H_2O$ | $CH_3COOH$ |
| "5:10" | 10.7 | 88.7 | 0 | 0.7 | | | |
| "21:15" | 10.4 | 89.0 | 0 | 0.6 | | | |
| "29:45" | 10.9 | 88.5 | 0 | 0.6 | 2.4 | 93.3 | 4.3 |

Table 2 shows the activity of the ODH catalyst towards converting ethanol to ethylene and acetic acid, determined from the average of product gas compositions (vol. %) at the three intervals and the final liquid composition (vol. %). It can be noted that the $CO_2$ content in the feed and product stream remains essentially unchanged.

TABLE 2

Catalyst Activity Towards Converting Ethanol to Ethylene and Acetic Acid

| Ethanol Conversion | Yield (C-atom wt. %) | | Selectivity (C-atom wt. %) | |
|---|---|---|---|---|
| (C-atom %) | $C_2H_4$ | $CH_3COOH$ | $C_2H_4$ | $CH_3COOH$ |
| 87 | 59 | 28 | 68 | 32 |

For these experiments, catalyst baseline activity was tested at typical ODH reaction conditions both before and after conducting the ethanol injection experiments. ODH conditions included a GHSV of 825 h$^{-1}$, a WHSV of 1.02 h$^{-1}$, a reactor inlet pressure of 18.3 psig, and a feed comprising 82 vol. % and 18 vol. % of ethane and oxygen, respectively. Injection of ethanol-steam for oxygen scavenging was found not to deactivate the catalyst, as shown in Table 3.

TABLE 3

Catalyst Baseline Activity Before and After Ethanol Injection Experiments

| | Ethane Conversion | $C_2H_4$ Yield (g$C_2H_4$/ | Selectivity (wt. %) | | | |
|---|---|---|---|---|---|---|
| | (wt. %) | gCat. hr) | $C_2H_4$ | $CO_2$ | CO | $CH_3COOH$ |
| Before | 13 | 0.09 | 91 | 2 | 3 | 5 |
| After | 13 | 0.09 | 91 | 2 | 3 | 5 |

In order to determine the amount of ethanol that will be required on a commercial scale to reduce oxygen concentration to about 10 ppm on dry basis, an Aspen simulation was conducted. The simulation was developed using ASPEN Plus® V10 software. PENG-ROB equation of state was used for the simulation. Steam properties were obtained using STEAMNBS. The reactor was modelled using RSTOIC model. The outlet stream composition after the ODH reaction was obtained from gPROMS® model and fed into ASPEN Plus. The reaction was performed at 152° C., similar to FBRU condition. The two reactions considered for ethanol conversion are:

$$C_2H_5OH+O_2 \rightarrow CH_3COOH+H_2O \tag{1}$$

$$C_2H_5OH \rightarrow C_2H_4+H_2O \tag{2}$$

The modules and equations used for the ASPEN simulation are known in the art. As used herein, PENG-ROB is the Peng Robinson equation of state, which expresses the fluid properties in terms of the critical properties and acentric factor of each species involved. STEAMNBS is the steam table used in ASPEN Plus to calculate the properties of steam. RSTOIC is a stoichiometric reactor model used in ASPEN Plus. This model is used when the reaction kinetics are unknown or unimportant but the stoichiometry and molar extent or conversion is known for each reaction. gPROMS is a software module from Process System Enterprise that is used to build, validate, and execute steady-state and dynamic process models.

Figure 4:
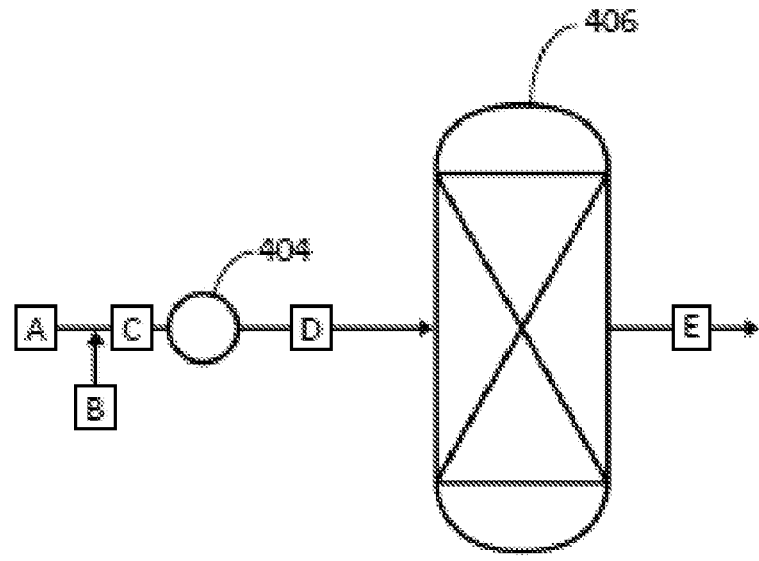
FIG. 4 is a flow diagram of components in a simulation for an oxygen removal reactor comprising an ODH catalyst.

Fractional conversion for each of the reaction steps was based on the yield provided in Table 3. The total conversion of ethanol is 87%. Based on the simulation, 241.8 kg/hr of ethanol is required for the polishing of the process gas stream containing 47.4 kg/hr of oxygen. The components of the model 400 are shown in FIG. 4 and include an oxygen removal reactor 406 and heat exchanger 404. A product stream A is mixed with an ethanol/water stream B to form a mixed stream C, which is passed through the heat exchanger 404 to form a cooled effluent stream D, which enters the oxygen removal reactor where the deoxygenated effluent E is formed. The composition and mass and heat balances of the compositions at each of points A through E are presented in in Table 4. The reactor heat duty was −0.43 GJ/hr.

TABLE 4

| Mass and Heat Balance for Model 400 | | | | | | |
| --- | --- | --- | --- | --- | --- | --- |
| Property | Units | A | B | C | D | E |
| Temperature | ° C. | 475.0 | 25.0 | 457.9 | 152.0 | 152.0 |
| Pressure | kPa | 317.0 | 332.0 | 317.0 | 302.0 | 287.0 |
| Molar Vapor Fraction | | 1.0 | 0.0 | 1.0 | 1.0 | 1.0 |
| Mass Density | kg/cum | 1.1 | 968.9 | 1.1 | 1.8 | 1.7 |
| Enthalpy Flow | GJ/hr | −1621.5 | −32.3 | −1653.8 | −1769.1 | −1769.6 |
| Average MW | | 20.6 | 19.3 | 20.5 | 20.5 | 20.5 |
| Mole Flows | kmol/hr | 8602.2 | 112.9 | 8715.1 | 8715.1 | 8718.2 |
| $CH_4$ | kmol/hr | 26.4 | 0.0 | 26.4 | 26.4 | 26.4 |
| $C_2H_6$ | kmol/hr | 365.9 | 0.0 | 365.9 | 365.9 | 365.9 |
| $C_2H_4$ | kmol/hr | 910.0 | 0.0 | 910.0 | 910.0 | 913.1 |
| $C_3H_8$ | kmol/hr | 8.5 | 0.0 | 8.5 | 8.5 | 8.5 |
| $CO_2$ | kmol/hr | 69.4 | 0.0 | 69.4 | 69.4 | 69.4 |
| CO | kmol/hr | 35.2 | 0.0 | 35.2 | 35.2 | 35.2 |
| $H_2O$ | kmol/hr | 7041.7 | 107.6 | 7149.3 | 7149.3 | 7153.9 |
| $CH_3COOH$ | kmol/hr | 143.6 | 0.0 | 143.6 | 143.6 | 145.1 |

TABLE 4-continued

| Mass and Heat Balance for Model 400 | | | | | | |
| --- | --- | --- | --- | --- | --- | --- |
| Property | Units | A | B | C | D | E |
| $O_2$ | kmol/hr | 1.5 | 0.0 | 1.5 | 1.5 | 0.0 |
| $C_2H_5OH$ | kmol/hr | 0.0 | 5.3 | 5.3 | 5.3 | 0.7 |

Example 2 (Removal of Oxygen/Acetylene with Cu/Zn Oxides Catalyst)

Removal of residual oxygen and acetylene using a Cu/Zn oxides catalyst was demonstrated using a lab scale oxidative dehydrogenation reactor termed a microreactor unit (MRU). The MRU reactor was formed from 0.5" O.D. stainless steel tubing and packed with 2 g of the ODH test catalyst. A feed comprising oxygen, ethane, and nitrogen at a weight ratio of 18 vol. %/36 vol. %/46 vol. %, respectively, was passed through the catalyst bed at 8.4 psig, at a gas flow rate of 32.8 sccm, and at a temperature of 327° C. Effluent from the MRU reactor was passed through a condenser allowing removal of an aqueous solution containing 18.5 wt. % acetic acid. The gaseous fraction, minus the condensed acetic acid, was passed to an oxygen removal reactor at 14 psig.

The oxygen removal reactor, a ¼" O.D. tube, was loaded with 1 g of the dried, calcined Cu/Zn/Zr oxides catalyst (powder form) and placed in a temperature control oven. The catalyst powder and the effluent gas were contacted at 150° C. at a pressure range of 8.4 psig to 4 psig, using a flow rate of 32.8 sccm. The effluent exited the oxygen removal reactor at ambient pressure and was evaluated using an Agilent® 6890N Gas Chromatograph, and the ChromPerfect®—Analysis, Version 6.1.10 software for data evaluation at several temperatures and time intervals. The results are provided in Table 5. Feed composition was measured at two different times to ensure consistency of GC measurements of the feed.

TABLE 5

| Experimental Results at Oxygen Removal Reactor Inlet Pressure Up to 14 psig | | | | | | | | | |
| --- | --- | --- | --- | --- | --- | --- | --- | --- | --- |
| | $C_2H_6$ (Vol-%) | $C_2H_4$ (Vol-%) | $O_2$ (Vol-%) | $CO_2$ (Vol-%) | $N_2$ (Vol-%) | CO (Vol-%) | $H_2$ (Vol-%) | $CH_4$ (Vol-%) | $C_2H_2$ (Vol-%) |
| Feed | 21.21 | 14.59 | 0.45 | 2.36 | 56.31 | 5.05 | 0.00 | 0.02 | 0.02 |
| Feed | 21.14 | 14.54 | 0.42 | 2.37 | 56.41 | 5.08 | 0.00 | 0.02 | 0.02 |
| Product | | | | | | | | | |
| 100° C. (1.5 hr) | 21.38 | 14.63 | 0.17 | 2.40 | 56.33 | 5.06 | 0.00 | 0.02 | 0.01 |
| 120° C. (2.5 hr) | 21.26 | 14.54 | 0.14 | 2.56 | 56.52 | 4.95 | 0.00 | 0.02 | 0.00 |
| 150° C. (3 hr) | 21.54 | 14.68 | 0.03 | 6.78 | 56.59 | 0.35 | 0.00 | 0.02 | 0.00 |
| 150° C. (3.5 hr) | 21.99 | 14.28 | 0.03 | 6.97 | 56.56 | 0.14 | 0.00 | 0.02 | 0.00 |
| 150° C. (14.5 hr) | 21.78 | 14.21 | 0.03 | 2.48 | 56.40 | 5.06 | 0.02 | 0.02 | 0.00 |
| 150° C. (14.5 hr) | 21.78 | 14.21 | 0.03 | 2.45 | 56.43 | 5.06 | 0.02 | 0.02 | 0.00 |
| 150° C. (15 hr) | 21.64 | 14.11 | 0.03 | 2.50 | 56.60 | 5.08 | 0.02 | 0.02 | 0.00 |

The data in Table 5 demonstrate that on the dried, calcined powder catalyst removes $O_2$, CO, and acetylene at temperatures of higher than 120° C. It is also clear form the data shown in Table 5 that all the compounds are not being chemosorbed but rather reacted either with oxygen from the catalyst or in the gas stream. The constant presence of oxygen in the feed stream was sufficient to oxidize all of the acetylene, which led to continuous removal of acetylene and $O_2$, even after the catalyst material was depleted of chemosorbed oxygen on the catalyst surface (as indicated by return of CO to original feed concentration).

Example 3 Aspen Simulation of Cu/Zn Oxide

A second ASPEN Plus simulation was conducted to determine requirements to run a polishing unit for removing acetylene in isothermal or adiabatic mode for a commercial plant. The simulation was developed using ASPEN Plus V10. PENG-ROB equation of state was used for the simulation. Steam properties were obtained using STEAMNBS. The reactor was modelled using RSTOIC model. The two reactions considered for the catalytic conversion are:

$$C_2H_2+2.5O_2 \rightarrow 2CO_2+H_2O \tag{1}$$

$$2CO+O_2 \rightarrow 2CO_2 \tag{2}$$

Figure 5:
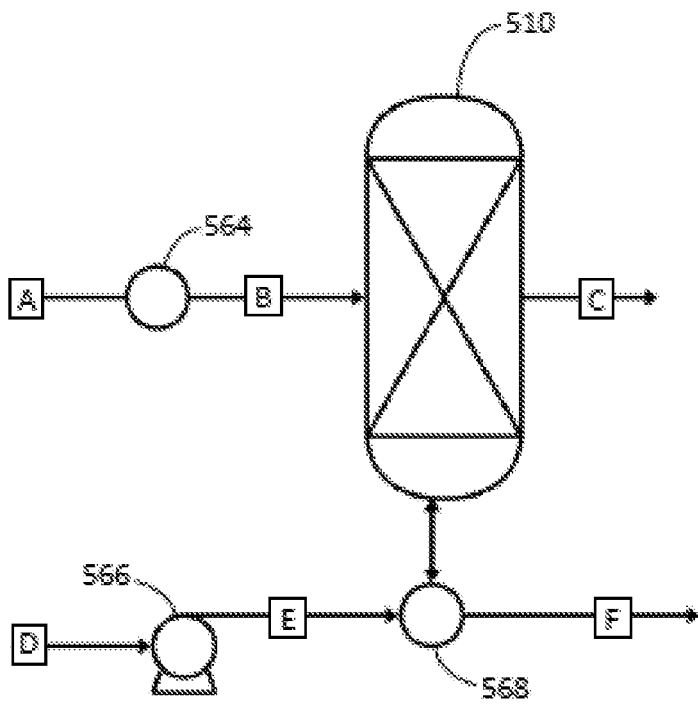
FIG. 5 is a flow diagram of components in a simulation for an oxygen removal reactor comprising a Cu/Zn oxide catalyst.

Model 500, shown in FIG. 5, includes an oxygen removal reactor 510 comprising a Cu/Zn oxide catalyst, a first heat exchanger 564, a pump 566, and a second heat exchanger 566. From the model 500, cooling water surrounding the oxygen removal reactor was modeled to control heat of the oxygen removal reactor 510 in conjunction with the second heat exchanger 568.

Adiabatic Operation of the Reactor

Modeling an adiabatic mode of oxygen removal water includes passing an effluent A (FIG. 5), similar to a deoxygenated effluent that was formed in a first oxygen removal reactor, through a heat exchanger 562 to form a heated effluent B that is introduced into the oxygen removal reactor 510 to form a polished gas stream C. The composition and mass and heat balances at each of points A, B, and C are shown in Table 6. By operating the reactor adiabatically, the required reaction temperature of 150° C. within the reactor (as noted by the temperature of the polished gas stream leaving the oxygen removal reactor) was achieved with a heated effluent B temperature of 141° C. It should be apparent to the person skilled in the art that routine optimization of the temperature, pressure, and flow of effluent A may be performed to provide for adiabatic operation similar that shown in this example. This includes various setups for compression, heating, and cooling downstream of a quench tower or scrubber. Results in Table 6 demonstrate the absence of oxygen and acetylene in the polished gas stream.

TABLE 6

| Mass and Heat Balances for Model 500 in Adiabatic Mode | | | | |
| --- | --- | --- | --- | --- |
| Property | Units | A | B | C |
| Temperature | ° C. | 94 | 141 | 150 |
| Pressure | kPa | 720 | 705 | 690 |
| Molar Vapor Fraction | | 1 | 1 | 1 |
| Mass Density | kg/cum | 7.1 | 6.1 | 5.8 |
| Enthalpy Flow | GJ/hr | −12.5 | −8.8 | −8.8 |
| Average MW | | 29.2 | 29.2 | 29.2 |
| Mole Flows | kmol/hr | 1417.3 | 1417.3 | 1416.6 |
| $CH_4$ | kmol/hr | 26.4 | 26.4 | 26.4 |
| $C_2H_6$ | kmol/hr | 365.9 | 365.9 | 365.9 |
| $C_2H_4$ | kmol/hr | 910.0 | 910.0 | 910.0 |
| $C_3H_8$ | kmol/hr | 8.5 | 8.5 | 8.5 |
| $CO_2$ | kmol/hr | 69.4 | 69.4 | 71.2 |
| CO | kmol/hr | 35.2 | 35.2 | 34.2 |
| $H_2O$ | kmol/hr | 0.0 | 0.0 | 0.4 |
| $CH_3COOH$ | kmol/hr | 0.0 | 0.0 | 0.0 |
| $O_2$ | kmol/hr | 1.5 | 1.5 | 0.0 |
| $N_2$ | kmol/hr | 0.0 | 0.0 | 0.0 |
| $C_2H_2$ | kmol/hr | 0.4 | 0.4 | 0.0 |

Isothermal Operation of the Reactor

A simulation for demonstration of an isothermal mode of oxygen removal using Model 500 and with cooling water circulation around the oxygen removal reactor includes, along with effluent A, heated effluent B, and polished gas C from the adiabatic mode, increasing pressure of cooling water D with pump 566 to form pressurized cooling water E, which via heat exchanger 568, cools water returning from cooling jacket of oxygen removal reactor 510 (double arrows) and to form heated cooling water F. Composition and mass and heat balances at each of points A through F are shown in Table 7. The results demonstrate that heated effluent B can enter the oxygen removal reactor 510 at a temperature of 150° C. provided the cooling water flow, temperature, and pressure can remove the reactor heat duty of 0.77 GJ/hr. In this example, the conditions of cooling water D in Table 7 were sufficient to remove the heat required for isothermal operation. The person skilled in the art would appreciate that pressure, temperature, and flow can be adjusted to provide isothermal operation similar to that shown in the example.

TABLE 7

| MHB for Isothermal Mode of Oxygen Scavenging Test Using Cu/Zn Oxides Catalyst | | | | | | | |
| --- | --- | --- | --- | --- | --- | --- | --- |
| Property | Units | A | B | C | D | E | F |
| Temperature | ° C. | 94 | 150 | 150 | 27 | 27 | 35 |
| Pressure | kPa | 705 | 690 | 665 | 150 | 515 | 500 |
| Molar Vapor Fraction | | 1 | 1 | 1 | 0 | 0 | 0 |
| Mass Density | kg/cum | 6.9 | 5.8 | 5.6 | 992.0 | 992.0 | 984.1 |
| Enthalpy Flow | GJ/hr | −12.5 | −8.0 | −8.8 | −335.2 | −335.2 | −334.4 |
| Average MW | | 29.2 | 29.2 | 29.2 | 18.0 | 18.0 | 18.0 |
| Mole Flows | kmol/hr | 1417.3 | 1417.3 | 1416.6 | 1165.7 | 1165.7 | 1165.7 |
| $CH_4$ | kmol/hr | 26.4 | 26.4 | 26.4 | 0.0 | 0.0 | 0.0 |
| $C_2H_6$ | kmol/hr | 365.9 | 365.9 | 365.9 | 0.0 | 0.0 | 0.0 |
| $C_2H_4$ | kmol/hr | 910.0 | 910.0 | 910.0 | 0.0 | 0.0 | 0.0 |
| $C_3H_8$ | kmol/hr | 8.5 | 8.5 | 8.5 | 0.0 | 0.0 | 0.0 |
| $CO_2$ | kmol/hr | 69.4 | 69.4 | 71.2 | 0.0 | 0.0 | 0.0 |
| CO | kmol/hr | 35.2 | 35.2 | 34.2 | 0.0 | 0.0 | 0.0 |
| $H_2O$ | kmol/hr | 0.0 | 0.0 | 0.4 | 1165.7 | 1165.7 | 1165.7 |
| ARGON | kmol/hr | 0.0 | 0.0 | 0.0 | 0.0 | 0.0 | 0.0 |
| $CH_3COOH$ | kmol/hr | 0.0 | 0.0 | 0.0 | 0.0 | 0.0 | 0.0 |
| $O_2$ | kmol/hr | 1.5 | 1.5 | 0.0 | 0.0 | 0.0 | 0.0 |
| $N_2$ | kmol/hr | 0.0 | 0.0 | 0.0 | 0.0 | 0.0 | 0.0 |
| $C_2H_2$ | kmol/hr | 0.4 | 0.4 | 0.0 | 0.0 | 0.0 | 0.0 |

Embodiments

An embodiment described in examples herein provides a method of converting ethane to ethylene. The method includes providing a feed stream including ethane and oxygen to an oxidative dehydrogenation reactor and converting at least a portion of the ethane to ethylene in the oxidative dehydrogenation reactor to provide a reactor effluent stream including ethane, ethylene, and oxygen, acetylene, or both. The method includes cooling the reactor effluent stream to form a cooled effluent stream and providing the cooled effluent stream to an oxygen removal reactor including an ODH catalyst bed. A deoxygenation stream including water and an alcohol is provided to the oxygen removal reactor to form a deoxygenated effluent.

In an aspect the method includes providing the deoxygenated effluent to an acetylene adsorption column.

In an aspect the method includes cooling the deoxygenated effluent to form a mixed effluent. In an aspect, the mixed effluent is separated into a gas stream and liquid stream. In an aspect, the gas stream is passed through a scrubber to remove acetic acid. In an aspect, the gas stream is compressed and provided to a cryogenic separation system to form a purified alkene stream.

In an aspect, the gas stream is compressed, heated, and then provided to a second oxygen removal reactor to form a polished gas stream. In an aspect, the polished gas stream is compressed and provided to a cryogenic separation system to form a purified alkene stream.

In an aspect, the gas stream is passed through a catalyst bed including copper, zinc, silver, chromium, cerium, or any combinations thereof in the second oxygen removal reactor to form the polished gas stream.

In an aspect, the method includes compressing the gas stream, heating the gas stream, and providing the gas stream to an acetylene adsorption column to form a polished gas stream. In an aspect, the method includes compressing the polished gas stream, and providing the polished gas stream to a cryogenic separation system to form a purified alkene stream.

In an aspect, the gas stream is passed through an adsorbent bed including copper, silver, or both, in the acetylene adsorption column to form the polished gas stream.

Another embodiment described in examples herein provides a system for forming ethylene from ethane. The system includes an oxidative dehydrogenation (ODH) reactor, a first heat exchanger to cool an ODH effluent from the ODH reactor, and an oxygen removal reactor including an ODH catalyst.

In an aspect, the system includes a second heat exchanger to cool an oxygen reduced effluent from the oxygen removal reactor, and a flash drum to separate the oxygen reduced effluent into a gas stream and a liquid stream. In an aspect, the system includes an acetic acid separation system on the liquid stream from the flash drum, the acetic acid separation system to separate the liquid stream into an acetic acid stream and a water stream. In an aspect, the system includes a scrubber that includes a water inlet to remove acetic acid from the gas stream in a counter current flow. In an aspect, the system includes a first compressor on the gas stream from the scrubber. In an aspect, the system includes a third heat exchanger to heat the gas stream from the compressor.

In an aspect, the system includes a polishing unit coupled to the third heat exchanger. In an aspect, the polishing unit includes a catalyst including copper, silver, zinc, or cerium, or any combinations thereof.

In an aspect, the polishing unit includes an acetylene adsorption column including an absorption bed including copper, silver, or zinc, or any combinations thereof. In an aspect, the system includes a second compressor on the gas stream from the first compressor. In an aspect, the system includes a cryogenic separation system coupled to the second compressor to form an alkene outlet stream.

Although this disclosure contains many specific embodiment details, these should not be construed as limitations on the scope of the subject matter or on the scope of what may be claimed, but rather as descriptions of features that may be specific to particular embodiments. Certain features that are described in this disclosure in the context of separate embodiments can also be implemented, in combination, in a single embodiment. Conversely, various features that are described in the context of a single embodiment can also be implemented in multiple embodiments, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular embodiments of the subject matter have been described. Other embodiments, alterations, and permutations of the described embodiments are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results.

Accordingly, the previously described example embodiments do not define or constrain this disclosure. Other changes, substitutions, and alterations are also possible without departing from the spirit and scope of this disclosure.

Other implementations are also within the scope of the following claims.

INDUSTRIAL APPLICABILITY

The present disclosure relates to the oxidative dehydrogenation of ethane into ethylene. More specifically, the present disclosure relates to removing oxygen from an ethane ODH product stream using ethanol.

The invention claimed is:

1. A method of converting ethane to ethylene comprising:
providing a feed stream comprising the ethane and oxygen to an oxidative dehydrogenation reactor;
converting at least a portion of the ethane to ethylene in the oxidative dehydrogenation reactor to provide a reactor effluent stream comprising ethane, ethylene, and one or both of oxygen and acetylene;
cooling the reactor effluent stream to form a cooled effluent stream;
providing the cooled effluent stream to an oxygen removal reactor comprising an ODH catalyst bed; and
providing a deoxygenation stream comprising water and ethanol to the oxygen removal reactor to form a deoxygenated effluent.

2. The method of claim 1, comprising providing the deoxygenated effluent to an acetylene adsorption column.

3. The method of claim 1, comprising cooling the deoxygenated effluent to form a mixed effluent.

4. The method of claim 3, comprising separating the mixed effluent into a gas stream and liquid stream.

5. The method of claim 4, comprising passing the gas stream through a scrubber to remove acetic acid.

6. The method of claim 4, comprising:

compressing the gas stream; and providing the gas stream to a cryogenic separation system to form a purified alkene stream.

7. The method of claim 4, comprising:

compressing the gas stream;

heating the gas stream; and providing the gas stream to a second oxygen removal reactor to form a polished gas stream.

8. The method of claim 7, comprising:

compressing the polished gas stream; and providing the polished gas stream to a cryogenic separation system to form a purified alkene stream.

9. The method of claim 7, comprising passing the gas stream through a catalyst bed comprising copper, zinc, silver, chromium, cerium, or any combinations thereof in the second oxygen removal reactor to form the polished gas stream.

10. The method of claim 4, comprising:

compressing the gas stream;

heating the gas stream; and providing the gas stream to an acetylene adsorption column to form a polished gas stream.

11. The method of claim 10, comprising:

compressing the polished gas stream; and providing the polished gas stream to a cryogenic separation system to form a purified alkene stream.

12. The method of claim 10, comprising passing the gas stream through an adsorbent bed comprising copper, silver, or both, in the acetylene adsorption column to form the polished gas stream.

13. A system for forming ethylene from ethane, comprising:

an oxidative dehydrogenation (ODH) reactor;

a first heat exchanger to cool an ODH effluent from the ODH reactor; and an oxygen removal reactor comprising an ODH catalyst.

14. The system of claim 13, comprising:

a second heat exchanger to cool an oxygen reduced effluent from the oxygen removal reactor; and a flash drum to separate the oxygen reduced effluent into a gas stream and a liquid stream.

15. The system of claim 14, comprising an acetic acid separation system on the liquid stream from the flash drum, the acetic acid separation system to separate the liquid stream into an acetic acid stream and a water stream.

16. The system of claim 14, comprising a scrubber comprising a water inlet to remove acetic acid from the gas stream in a counter current flow.

17. The system of claim 16, comprising a first compressor on the gas stream from the scrubber.

18. The system of claim 17, comprising a third heat exchanger to heat the gas stream from the compressor.

19. The system of claim 18, comprising a polishing unit coupled to the third heat exchanger.

20. The system of claim 19, wherein the polishing unit comprises a catalyst comprising catalyst including copper, silver, zinc, or cerium, or any combinations thereof.

21. The system of claim 19, wherein the polishing unit comprises an acetylene adsorption column comprising an absorption bed comprising copper, silver, or zinc, or any combinations thereof.

22. The system of claim 17, comprising a second compressor on the gas stream from the first compressor.

23. The system of claim 22, comprising a cryogenic separation system coupled to the second compressor to form an alkene outlet stream.

* * * * *